United States Patent [19]

Clementi

[11] Patent Number: 5,031,612
[45] Date of Patent: Jul. 16, 1991

[54] SYSTEM AND METHOD FOR DELIVERING WARM HUMIDIFIED AIR

[75] Inventor: Fancis J. Clementi, Munhall, Pa.

[73] Assignee: DeVilbiss Health Care, Inc., Somerset, Pa.

[21] Appl. No.: 513,923

[22] Filed: Apr. 24, 1990

[51] Int. Cl.⁵ .............................................. A61M 16/16
[52] U.S. Cl. ............................ 128/204.14; 128/204.17; 261/DIG. 31
[58] Field of Search ............... 128/911, 203.17, 204.17, 128/204.13, 201.13, 204.14, 203.26, 203.27; 261/DIG. 31, DIG. 15, DIG. 37, DIG. 65

[56] References Cited

U.S. PATENT DOCUMENTS

| | | | |
|---|---|---|---|
| 437,070 | 9/1890 | Wiesebrock | 128/203.26 |
| 3,510,252 | 5/1970 | Reich | 261/DIG. 34 X |
| 3,616,796 | 6/1971 | Jackson | 128/212 |
| 3,638,926 | 2/1972 | Melville et al. | 261/130 |
| 3,945,378 | 3/1976 | Paluch | 128/145.8 |
| 4,048,993 | 9/1977 | Dobritz | 261/DIG. 65 X |
| 4,369,777 | 1/1983 | Lwoff et al. | 128/203.27 X |
| 4,621,632 | 11/1986 | Bartels et al. | 128/203.27 |
| 4,621,633 | 11/1986 | Bowles et al. | 128/203.27 X |
| 4,637,384 | 1/1987 | Schroeder | 128/204.18 |
| 4,722,334 | 2/1988 | Blackmer et al. | 128/203.16 |
| 4,773,410 | 9/1988 | Blackmer et al. | 128/203.26 |
| 4,967,744 | 11/1990 | Chua | 128/204.18 |

FOREIGN PATENT DOCUMENTS 210601 6/1909 Fed. Rep. of Germany ........................ 128/203.26

Primary Examiner—Clifford D. Crowder
Assistant Examiner—Eric P. Raciti
Attorney, Agent, or Firm—MacMillan, Sobanski & Todd

[57] ABSTRACT

A system for delivering warm humidified air to a patient. Pressurized air is heated to a predetermined temperature and a portion of the heated air is humidifed to substantially 100% relative humidity. The warm humidified air is delivered to a patient through an inner one of a pair of coaxial hoses. The remaining heated air is passed through an annular passage between the two hoses to maintain the temperature and vapor content of the warm humidified air delivered to the patient.

10 Claims, 1 Drawing Sheet ized air is delivered by a blower 11 to a hose 12 which contains an in line electric heating element 13. A temperature sensor 14 is located in the hose 12 downstream from the heating element 13. A temperature control circuit 15 is responsive to a preset temperature and to the sensor 14 for supplying power to the heating element 13 to heat the air flowing through the hose 12 to the preset temperature.

SYSTEM AND METHOD FOR DELIVERING WARM HUMIDIFIED AIR

TECHNICAL FIELD

The invention relates to a system and a method for delivering warm humidified air to a patient and more particularly to a system and a method for maintaining the temperature of the warm humidified air as it is delivered to the patient.

BACKGROUND ART

It is sometimes desirable to treat a patient having respiratory problems with air or another gas which is warmed and humidified. The air may be room air delivered under pressure by a blower or air delivered by a positive pressure ventilator. Typically, pressurized air is heated and humidified and then delivered through a hose and either a cannula or a mask to the patient's respiratory tract. For some treatments, it is desirable to saturate the air with water vapor. In some cases, the air also may be enriched with oxygen prior to humidification.

When a heated gas is humidified to a high relative humidity, there are problems in delivering the gas to the patient. If the humidified gas cools as it is delivered to the patient, a portion of the vapor will condense on the walls of the delivery hose. Consequently, the gas will not be delivered to the patient at the desired temperature and with the desired vapor content. It is known, for example, from U.S. Pat. No. 3,638,926, that the delivery hose may have an embedded helical electric heater wire for heating the gas as it is delivered. However, it is difficult to accurately control the heating wire to maintain the temperature and saturation level of the gas constant as the gas flows through the hose. Condensation may occur at any cooler point on the hose.

It is also known that two coaxial hoses may be used for delivering to a patient a gas containing an anesthetic vapor. As is taught in U.S. Pat. No. 4,637,384, the gas and anesthetic vapor are delivered through an inner one of the hoses. Exhaled gases flow through an outer annular passage which surrounds the inner hose to carry such gases away from the patient. It does not appear that the delivered gas and anesthetic vapors are heated and the exhaled gases are not used to maintain the temperature of the gas and anesthetic vapors being delivered to the patient.

U.S. Pat. No. 3,616,796 teaches the delivery of heated humidified gas to a patient using two coaxial hoses. The gas is delivered through the inner one of the hoses which is water permeable. Heated water is passed through the outer annular passage. The heated water heats the delivered gas and water which permeates the inner tube humidifies the gas. This system has no control over the level that the gas is humidified.

DISCLOSURE OF INVENTION

According to the invention, an improved system and method are provided for delivering warm humidified air or other vapor containing gas to a patient without loss of temperature and with minimal or no condensation in the gas as it is delivered. The gas is heated prior to humidification. Only a portion of the heated gas is humidified and delivered to the patient through the inner one of two coaxial hoses. A remaining portion of the heated gas is discharged to atmosphere through an annular passage which surrounds the inner hose. The surrounding flow of heated gas maintains the temperature of the humidified gas as it flows to the patient, thereby preventing or minimizing condensation. Consequently, when the gas is heated to a prescribed temperature and is humidified to a prescribed relative humidity up to saturation, the patient is assured of receiving the gas at such prescribed temperature and humidity.

Accordingly, it is an object of the invention to provide an improved system and method for delivering a warm humidified gas to a patient.

Other objects and advantages of the invention will be apparent from the following description and the accompanying drawings.

BRIEF DESCRIPTION OF THE DRAWINGS

The single figure is a pictorial diagram illustrating a system according to the invention for delivering warm humidified air to a patient.

BEST MODE FOR CARRYING OUT THE INVENTION

Figure 1:
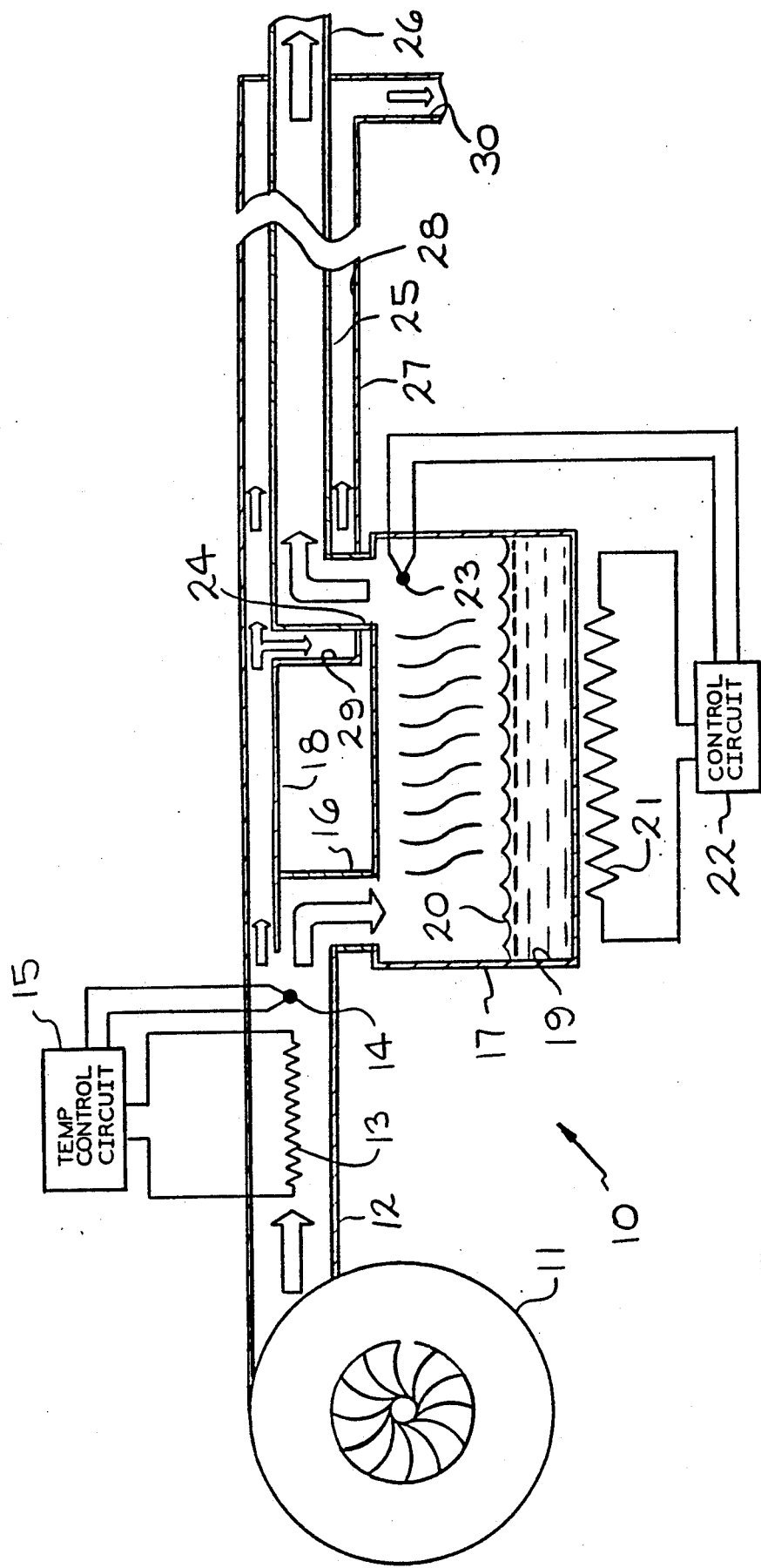

Referring now to the attached drawing, a system 10 is shown according to the invention for delivering warm humidified air to a patient at a desired temperature and humidity. Pressurized air is delivered by a blower 11 to a hose 12 which contains an in line electric heating element 13. A temperature sensor 14 is located in the hose 12 downstream from the heating element 13. A temperature control circuit 15 is responsive to a preset temperature and to the sensor 14 for supplying power to the heating element 13 to heat the air flowing through the hose 12 to the preset temperature.

Downstream of the temperature sensor 14, the heated air flowing through the hose 12 is split into two streams. A major portion of the heated air flows through a hose 16 to a humidifier 17 and a lesser portion of the heated air flows to a hose 18. The humidifier 17 may be of any conventional design, including a heated liquid vaporizer or a nebulizer (not shown). The illustrated humidifier 17 consists of a reservoir 19 holding a volume of water 20. An electric heating element 21 is operated by a control circuit 22 to heat the water 20. The circuit 22 is responsive to a feedback signal from a temperature sensor 23 located to sense the air temperature in the humidifier 17 above the water 20 and adjacent an air outlet 24 to maintain the humidifier water 20 at a desired temperature to obtain a prescribed humidity in the air at the outlet 24.

Warm humidifier air is delivered from the air outlet 24 through a hose 25 to an air discharge point 26. The warm air at the discharge point 26 may be humidified up to saturation, i.e., up to 100 percent relative humidity. The discharge point 26 may be connected, for example, through a cannula (not shown) or a mask (not shown) to deliver the gas to a patient's nostrils. Since the hose 25 may be of some length, a second hose 27 is positioned coaxial to the hose 25. An annular passage 28 is formed between the hoses 25 and 27 preferably to extend substantially the entire length of the hose 25. The annular passage 28 has an inlet end 29 adjacent the humidifier air outlet 24 and has an outlet end 30 adjacent the warm humidified air discharge point 26. The hose 18 is connected to the passage inlet end 29 and the passage outlet end 30 is vented to atmosphere. Consequently, the portion of the heated air in the hose 12 which was not passed through the humidifier 17 is discharged through the hose 18, the annular passage 28 and the outlet 30 to atmosphere. Since the air surrounding the hose 25 is at the same temperature as the air delivered to the humidifier 17, the warm humidified air delivered through the hose 25 is insulated against heat loss. Consequently, the air reaching the patient will have the desired temperature and may be humidified up to the saturation point with little or no condensation as it passes through the hose 25.

It will be appreciated that various known types of vaporizers and humidifiers may be used in the system 10. The source of pressurized air for the system 10 may be the illustrated blower 11 or it may be other known respiratory gas sources such as a positive pressure ventilator. Further, it will be appreciated that liquids other than water may be vaporized and delivered with a heated gas to a patient by the system 10. Various other modifications and changes may be made to the above described embodiment of the invention without departing from the spirit and the scope of the following claims.

I claim:

1. A system for delivering warm humidified air to a patient comprising, in combination, means for heating air to a desired temperature, means for humidifying at least a portion of such heated air, means for delivering at least a portion of such humidified heated air to the patient, and means using a remaining portion of the heated air not delivered to the patient to maintain the temperature of the humidified heated air substantially constant as it is delivered to the patient, whereby there is no substantial change in the humidity of the heated humidified air as it is delivered to the patient.

2. A system for delivering warm humidified air to a patient, as set forth in claim 1, wherein said means for delivering such humidified heated air to the patient includes a delivery hose.

3. A system for delivering warm humidified air to a patient, as set forth in claim 2, wherein said means for maintaining the temperature of the humidified heated air as it is delivered to the patient includes means for surrounding said delivery hose with the remaining portion of the heated air used to maintain the temperature.

4. A system for delivering warm humidified air to a patient, as set forth in claim 2, wherein said means for maintaining the temperature of the humidified heated air as it is delivered to the patient includes a second hose positioned coaxial with said delivery hose, said second hose forming an annular passage surrounding said delivery hose, and means for passing the remaining portion of the heated air used to maintain the temperature through said annular passage.

5. A system for delivering warm humidified air to a patient, as set forth in claim 2, wherein said means for humidifying at least a portion of such heated air includes means for humidifying such portion of heated air to substantially 100 percent relative humidity.

6. A system for delivering to a patient a warm gas containing a vapor comprising, in combination, means for heating such gas to a desired temperature, means for adding a vapor to at least a portion of such heated gas, means for delivering at least a portion of such heated gas and vapor to the patient, and means using a remaining portion of the heated gas not delivered to the patient to maintain the temperature of such heated gas and vapor whereby there is no substantial change in the saturation of the heated gas and vapor as they are delivered to he patient.

7. A system for delivering to a patient a warm gas containing a vapor, as set forth in claim 6, wherein said means for adding a vapor includes means for saturating with the vapor such portion of heated gas to which the vapor is added.

8. A method of delivering warm humidified air to a patient comprising the steps of:
 (a) heating air to a desired temperature;
 (b) humidifying at least a portion of said heated air;
 (c) delivering at least a portion of said humidified heated air to the patient; and
 (d) using a remaining portion of said heated air not delivered to the patient to maintain the temperature of said humidified heated air substantially constant as it is delivered to the patient whereby there is not substantial change in the humidity of the heated humidified air as it is delivered to the patient.

9. A method for delivering warm humidified air to a patient, as set forth in claim 8, wherein said delivered humidified heated air is delivered through an inner one of a pair of coaxial hoses, and wherein such remaining portion of the heated air used to maintain the temperature is passed through an annular passage between said coaxial hoses to maintain the temperature of said delivered humidified air as it is delivered to the patient.

10. A method for delivering warm humidified air to a patient, as set forth in claim 9, wherein said heated air is humidified to substantially 100 percent relative humidity.

* * * * *

UNITED STATES PATENT AND TRADEMARK OFFICE
CERTIFICATE OF CORRECTION

PATENT NO. : 5,031,612
DATED : July 16, 1991
INVENTOR(S) : Francis J. Clementi It is certified that error appears in the above-identified patent and that said Letters Patent is hereby corrected as shown below:

On the title page of U.S. Patent No. 5,031,612, please change the inventor's name from "Fancis" to read -- Francis --.

Signed and Sealed this

Seventeenth Day of November, 1992

*Attest:*

DOUGLAS B. COMER

*Attesting Officer*  *Acting Commissioner of Patents and Trademarks*